United States Patent [19]

Szmuszkovicz

[11] Patent Number: 4,978,753
[45] Date of Patent: Dec. 18, 1990

[54] 7-PHENYLPYRIMIDO[1,2-ALPHA][1,4]BEN-ZODIAZEPIN-3(5H)-ONES

[75] Inventor: Jacob Szmuszkovicz, Kalamazoo, Mich.

[73] Assignee: The Upjohn Company, Kalamazoo, Mich.

[21] Appl. No.: 430,751

[22] Filed: Nov. 2, 1989

Related U.S. Application Data

[63] Continuation of Ser. No. 323,765, Jan. 15, 1973, abandoned.

[51] Int. Cl.$^5$ .............................................. C07D 487/08
[52] U.S. Cl. .................................. 540/559; 540/571; 540/572
[58] Field of Search ........................................ 540/559

[56] References Cited

U.S. PATENT DOCUMENTS

| | | |
|---|---|---|
| 3,734,912 | 5/1973 | Hanze et al. ................ 260/256.5 R |
| 3,987,052 | 10/1976 | Hester, Jr. ...................... 260/308 R |
| 4,175,079 | 11/1979 | Kuwada et al. ................... 260/243.3 |

OTHER PUBLICATIONS

Kuwada et al., "Chemical Abstracts", vol. 79, 1973, Col. 32117r.
Szmuszkovicz, "Chemical Abstracts", vol. 81, 1974, Col. 120717h.
"Chemical Abstracts", vol. 83, 1975, Col. 179150m.
Natsugari et al., "Chemical Abstracts", vol. 93, 1980, Col. 93:26405f.
Freidinger et al., "Chemical Abstracts", vol. 110, 1989, Col. 110:173266j.

Primary Examiner—Glennon H. Hollrah
Assistant Examiner—James H. Turnipseed
Attorney, Agent, or Firm—Sidney B. Williams, Jr.

[57] ABSTRACT

A 7-phenylpyrimido[1,2-a][1,4]benzodiazepin-3(5H)-ones of the formula II:

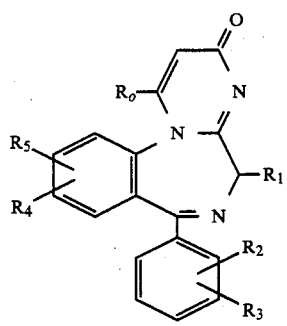

wherein $R_o$ is selected from the group consisting of hydrogen, alkyl of 1 to 3 carbon atoms, inclusive, —COOR in which R is alkyl defined as above,

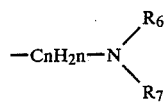

in which n is a number of 1 to 4, $R_6$ and $R_7$ are hydrogen or alkyl defined as above or together

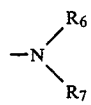

is selected from the group consisting of pyrrolidino, piperidino, morpholino, and 4-methylpiperazino, and —CH$_2$OH; wherein $R_1$ is selected from the group consisting of hydrogen, hydroxy, acetoxy, propionoxy, succinyloxy, and alkyl esters thereof; wherein $R_2$, $R_3$, $R_4$, and $R_5$ are selected from the group consisting of hydrogen, halogen, nitro, cyano, trifluoromethyl, lower-alkyl, -alkoxy, -alkylthio, -alkylsulfinyl, -alkylsulfonyl, -alkanoylamino and -dialkylamino, are synthesized by condensing a 2-amino-5-phenyl-3H-1,4-benzodiazepine of the formula I

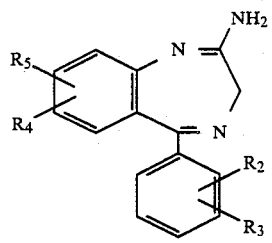

with a compound selected from the group consisting of acetylenic compounds of the formulae HC≡C—COOR, ROOC≡C—COOR in which R is alkyl defined above, inclusive, and

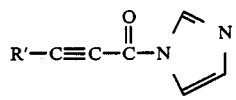

in which R' is alkyl defined as above or

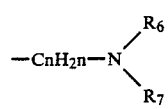

defined as above, to give a compound of formula IIa (Abstract continued on next page.)

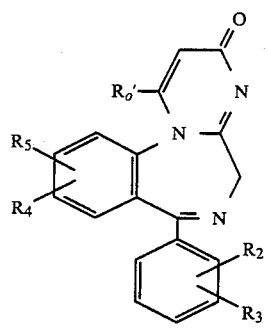

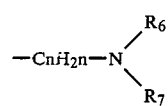

wherein $R_2$, $R_3$, $R_4$, and $R_5$ is defined as above, and $R_o'$ is selected from the group consisting of hydrogen, alkyl as defined above, —COOR as defined above, and as defined above. Compounds of formula II wherein $R_o$ is —CH$_2$OH are obtained by reducing a compound IIa wherein $R_o$ is —CH$_2$OH are obtained by reducing a compound IIa wherein $R_o'$ is —COOR.

The compounds of formula II and their pharmacologically acceptable acid addition salts and N-oxides are useful tranquilizers and sedatives for birds and mammals.

23 Claims, No Drawings

7-PHENYLPYRIMIDO[1,2-ALPHA][1,4]BENZODIAZEPIN-3(5H)-ONES

CROSS-REFERENCE TO RELATED APPLICATIONS

The present application is a continuation application of Ser. No. 323,765 filed Jan. 15, 1973, now abandoned.

BACKGROUND OF THE INVENTION

Field of the Invention

This invention is directed to new organic compounds and is particularly concerned with novel 7-phenyl-pyrimido[1,2-a][1,4]benzodiazepin-3(5H)-ones (II) and the process therefor. The invention furthermore includes the pharmaceutically acceptable acid addition salts.

The novel compounds II, intermediates, and the process of production thereof can be illustratively represented as follows:

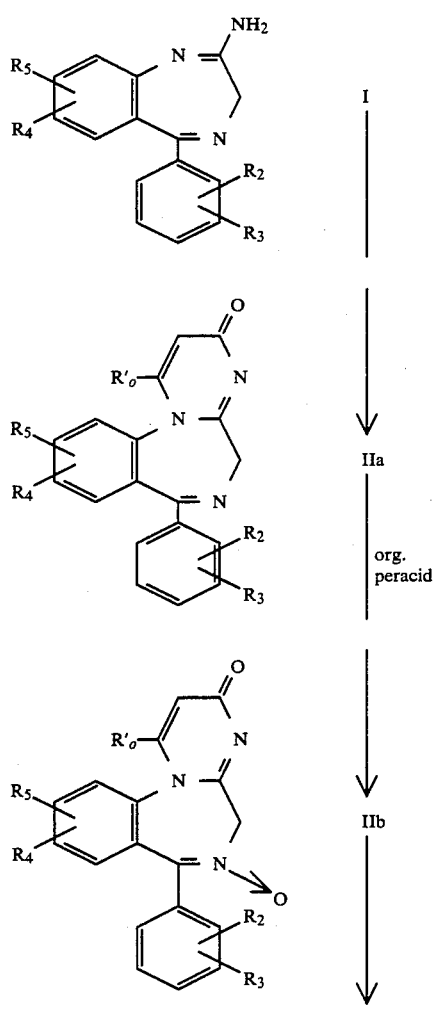

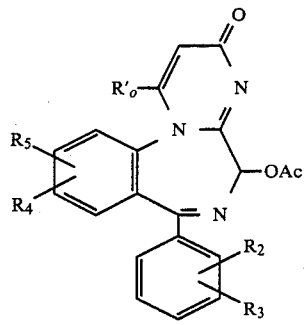

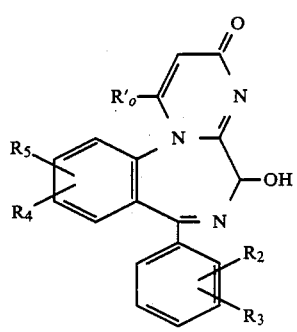

wherein $R'_0$ is selected from the group consisting of hydrogen, alkyl of 1 to 3 carbon atoms, inclusive, —COOR in which R is alkyl defined as above, and

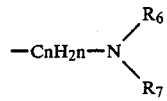

in which n is a number from 1 to 4, $R_6$ and $R_7$ are alkyl defined as above, or together

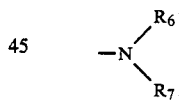

is selected from the group consisting of pyrrolidino, piperidino, morpholino, and 4-methylpiperazino; wherein $R_1$ is selected from the group consisting of hydrogen, hydroxy, acetoxy, propionoxy, hydrogen succinyloxy, and alkylsuccinyloxy in which alkyl is defined as above; wherein $R_2$, $R_3$, $R_4$, and $R_5$ are selected from the group consisting of hydrogen, halogen, nitro, cyano, trifluoromethyl, and alkyl, alkoxy, alkylthio, alkylsulfinyl, alkylsulfonyl, and alkanoylamino in which the carbon moiety is of 1 to 3 carbon atoms, inclusive, and dialkylamino in which alkyl is defined as above, and Ac is acetyl.

The compounds wherein $R_0$ is hydroxymethyl are produced from those wherein $R_0'$ is —COOR (R being alkyl of 1 to 3 carbon atoms, inclusive) by selective reduction with lithium aluminum hydride.

The preferred product of this invention are those of the formula IIe:

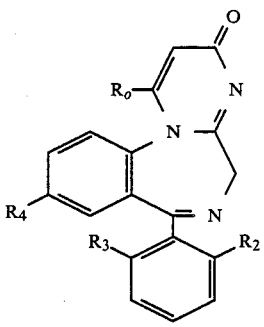

IIe wherein R₀ is defined as above; and wherein R₂, R₃, and R₄ are selected from the group consisting of hydrogen, fluorine, chlorine, bromine, nitro, trifluoromethyl, and alkylthio in which alkyl is of 1 to 3 carbon atoms, inclusive.

More preferred still are those compounds of formula IIf:

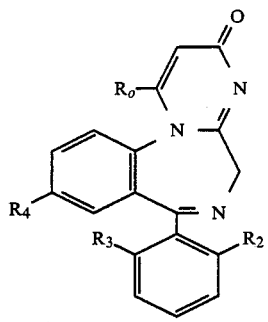

IIf wherein R₀ is defined as above and R₂, R₃, and R₄ are selected from the group consisting of hydrogen and chlorine.

Furthermore this invention includes the compound of formula II (which formula includes the subspecies IIa, IIb, IIc, IId, IIe, and IIf) as acid addition salts of pharmacologically acceptable acids. Both, the free base and the pharmacologically acceptable acid addition salts are useful as tranquilizing and sedative agents.

The basic process of this invention comprises: the formation of the pyrimido ring by reaction of an amine of formula I with a reagent selected from the group consisting of HC≡C—COOR, ROOC—C≡C—COOR in which R is alkyl as defined above and

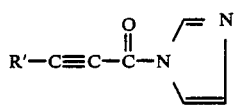

in which R' is alkyl as defined above or

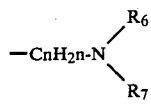

in which n, R₆, and R₇ are defined as above.

DESCRIPTION OF THE PREFERRED EMBODIMENT

Lower alkyl groups of 1 to 3 carbon atoms, inclusive, are exemplified by methyl, ethyl, propyl, and isopropyl.

The carbon chain moieties of alkoxy, alkylthio, alkylsulfinyl, alkylsulfonyl, and dialkylamino is defined as alkyl of 1 to 3 carbon atoms, inclusive, as above.

The alkanoylamino group with an alkane moiety of 1 to 3 carbon atoms, inclusive, consists of formamido, acetamido, and propionamido.

The term halogen includes fluorine, chlorine, bromine, and iodine.

The novel compounds of the formula II comprising compounds IIa, IIb, IIc, IId, IIe, and IIf and including acid addition salts and N-oxides thereof have sedative, tranquilizing, hypnotic, anticonvulsant, anti-anxiety, anti-depressant, and muscle relaxant effects in mammals and birds.

The acid addition salts of compounds of formula II contemplated in this invention, are the hydrochlorides, hydrobromides, hydroiodate, sulfates, phosphates, cyclohexanesulfamates, β-naphthalenesulfonates, methanesulfonates, ethanesulfonates, benzenesulfonates, toluenesulfonates, and the like, prepared by reacting a compound of formula II with the stoichiometrically calculated amount of the selected pharmacologically acceptable acids.

The compounds (II) of this invention were screened in mice by standard procedures such as chimney, pedestal, and dish test and also as antagonist to strychnine, nicotine, and metrazol. These tests showed that the compounds of formula II were excellent as sedatives, hypnotics, tranquilizers, anti-anxiety, anti-convulsives, and muscle relaxants and could be administered orally or parenterally to mammals, such as man, domestic pet animals, e.g. dogs, cats, monkeys, or pet birds, such as parrots. They are also useful during the transportation of cattle, sheep, swine, or zoo animals of the mammal and/or bird class.

The pharmaceutical forms contemplated by this invention include pharmaceutical compositions suited for oral, parenteral, and rectal use, e.g., tablets, powder packets, cachets, dragees, capsules, solutions, suspensions, sterile injectable forms, suppositories, bougies, and the like. Suitable diluents or carriers such as carbohydrates (lactose), proteins, lipids, calcium phosphate, cornstarch, stearic acid, methylcellulose and the like may be used as carriers or for coating purposes. Water or oil, e.g., coconut oil, sesame oil, safflower oil, cottonseed oil, peanut oil may be used for preparing solutions or suspensions of the active drug. Sweetening, coloring, and flavoring agents may be added.

For mammals and birds, food premixes with starch, oatmeal, dried fishmeat, fishmeal, flour, and the like can be prepared.

As tranquilizer; the compounds of formula II and their pharmacologically acceptable acid addition salts can be used in dosages of 0.01–2.0 mg./kg., preferably in a dosage of 0.05–0.5 mg./kg. in oral or injectable preparations, as described above, to alleviate tension and anxiety in mammals, or birds, such as e.g., occurs when animals are in travel.

Other acid addition salts of the compounds of formula II can be made such as the fluosilicic acid addition salts which are useful mothproofing compounds or the trichloroacetates useful as herbicides against Johnson grass, Bermuda grass, yellow foxtail and green foxtail, and quack grass.

The starting compounds used in this invention are 2-amino-5-phenyl-3H-1,4-benzodiazepines (I). These amines (I) are prepared from the well-known 1,3-dihydro-5-phenyl-2H[1,4]benzodiazepine-2-thiones [Archer et al., J. Org. Chem. 29, 231 (1964) and U.S. Pat. No. 3,422,091] by treatment of such thiones with ammonia in methanol. Details of this reaction are shown in Preparation 1.

Representative 2-amino compounds of formula I thus produced include;
2-amino-5-phenyl-3H-1,4-benzodiazepine;
2-amino-7-chloro-5-phenyl-3H-1,4-benzodiazepine;
2-amino-6-chloro-5-(m-bromophenyl)-3H-1,4-benzodiazepine;
2-amino-8-chloro-5-(o-chlorophenyl)-3H-1,4-benzodiazepine;
2-amino-7-bromo-5-phenyl-3H-1,4-benzodiazepine;
2-amino-7-chloro-5-(3,4-dimethylphenyl)-3H-1,4-benzodiazepine;
2-amino-5-(2-methyl-4-methoxyphenyl)-3H-1,4-benzodiazepine;
2-amino-7-methyl-5-phenyl-3H-1,4-benzodiazepine;
2-amino-7-nitro-5-phenyl-3H-1,4-benzodiazepine;
2-amino-7-nitro-5-(o-chlorophenyl)-3H-1,4-benzodiazepine;
2-amino-7-fluoro-5-phenyl-3H-1,4-benzodiazepine;
2-amino-7-chloro-5-(2,6-difluorophenyl)-3H-1,4-benzodiazepine;
2-amino-7-trifluoromethyl-5-phenyl-3H-1,4-benzodiazepine;
2-amino-9-trifluoromethyl-5-[p-(propionylamino)phenyl]-3H-1,4-benzodiazepine;
2-amino-7-cyano-5-phenyl-3H-1,4-benzodiazepine;
2-amino-8-cyano-5-[p-(trifluoromethyl)phenyl]-3H-1,4-benzodiazepine;
2-amino-7-chloro-5-(o-chlorophenyl)-3H-1,4-benzodiazepine;
2-amino-6-ethylthio-5-(o-bromophenyl)-3H-1,4-benzodiazepine;
2-amino-6,8-dichloro-5-(o-fluorophenyl)-3H-1,4-benzodiazepine;
2-amino-8-propoxy-7-bromo-5-[m-(ethylsulfinyl)phenyl]-3H-1,4-benzodiazepine;
2-amino-9-diisopropylamino-7-methyl-5-[m-(propylsulfonyl)phenyl]-3H-1,4-benzodiazepine;
2-amino-7-bromo-5-(o-fluorophenyl)-3H-1,4-benzodiazepine;
2-amino-8-methyl-5-(o-fluorophenyl)-3H-1,4-benzodiazepine;
2-amino-9-iodo-5-(o-fluorophenyl)-3H-1,4-benzodiazepine;
2-amino-7-chloro-5-(2,6-difluorophenyl)-3H-1,4-benzodiazepine;
2-amino-7-trifluoromethyl-5-phenyl-3H-1,4-benzodiazepine;
2-amino-8-methyl-5-(p-fluorophenyl)-3H-1,4-benzodiazepine;
2-amino-7-nitro-5-(o-iodophenyl)-3H-1,4-benzodiazepine;
2-amino-5-(o-chlorophenyl)-3H-1,4-benzodiazepine;
2-amino-7-bromo-5-(o-bromophenyl)-3H-1,4-benzodiazepine;
2-amino-7-methylsulfinyl-5-(o-fluorophenyl)-3H-1,4-benzodiazepine;
2-amino-7-methyl-5-(o-chlorophenyl)-3H-1,4-benzodiazepine;
2-amino-7-methylthio-5-phenyl-3H-1,4-benzodiazepine;
2-amino-7-cyano-5-(o-chlorophenyl)-3H-1,4-benzodiazepine;
2-amino-6,8-dimethyl-5-(o-chlorophenyl)-3H-1,4-benzodiazepine;
2-amino-9-propylsulfonyl-7-methyl-5-phenyl-3H-1,4-benzodiazepine;
2-amino-7-trifluoromethyl-5-(o-chlorophenyl)-3H-1,4-benzodiazepine;
2-amino-7-dimethylamino-5-phenyl-3H-1,4-benzodiazepine;
2-amino-7-fluoro-5-(o-chlorophenyl)-3H-1,4-benzodiazepine;
2-amino-7,8-dicyano-5-[p-(methylsulfonyl)phenyl]-3H-1,4-benzodiazepine;
2-amino-6,9-dichloro-5-(p-isopropylphenyl)-3H-1,4-benzodiazepine;
2-amino-6-methoxy-5-(2,4-diethoxyphenyl)-3H-1,4-benzodiazepine;
2-amino-9-acetamido-5-[p-(trifluoromethyl)phenyl]-3H-1,4-benzodiazepine;
2-amino-6,8-diethyl-5-(m-ethylphenyl)-3H-1,4-benzodiazepine;
2-amino-6-nitro-5-(o-cyanophenyl)-3H-1,4-benzodiazepine;
2-amino-7,9-bis(dipropylamino)-5-(o-nitrophenyl)-3H-1,4-benzodiazepine;
2-amino-9-acetylamino-5-(p-cyanophenyl)-3H-1,4-benzodiazepine;
and the like.

In carrying out the process of the invention, a selected 2-amino-5-phenyl-3H-1,4-benzodiazepine (I) is reacted (Method I) in an inert organic solvent with a lower-alkyl ester of propiolic acid of the formula $$HC{\equiv}C-COOR \qquad IV$$

wherein R is an alkyl group of 1 to 3 carbon atoms inclusive to produce compounds of formula IIa in which $R'_o$ is hydrogen; or (Method II) a dialkyl acetylenedicarboxylate of the formula $$ROOC-C{\equiv}C-COOR \qquad V$$

wherein R is an alkyl group of 1 to 3 carbon atoms, inclusive, to produce compounds of formula IIa in which $R'_o$ is —COOR which can be decarboxylated after hydrolysis with lithium iodide in pyridine to give IIa in which $R'_o$ is hydrogen, or which is carefully reduced with lithium aluminum hydride to give II in which $R_o$ is hydroxymethyl; or (Method III) an imidazole amide of the formula

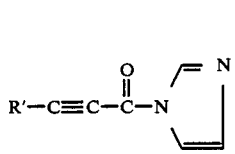

VI wherein R' is alkyl of 1 to 3 carbon atoms or

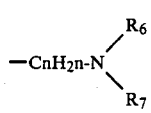

in which n is 1 to 4 and $R_6$ and $R_7$ are each selected from the group consisting of hydrogen and alkyl of 1 to 3 carbon atoms or

together is pyrrolidino, piperidino, 4-methylpiperazino, and morpholino to give IIa in which $R_o$ is alkyl of 1 to 3 carbon atoms or

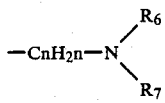

in which n is 1 to 4 and $R_6$ and $R_7$ are as defined above.

This reagent VI can be produced in situ by employing carbonyldiimadazole and a propiolic acid of the formula

$$R-C\equiv C-COOH$$

wherein R is alkyl defined as above.

Solvents useful in this reaction include the lower alkanols of 1 to 6 carbon atoms e.g. methanol, ethanol, propanol, hexanol, and solvents such as tetrahydrofuran, cyclohexane, benzene, toluene, and mixtures thereof and the like.

The reaction can be carried out between 20° and the reflux temperature of the mixture depending on the solvents i.e. between 65°–145° C.

The reagents are generally mixed in about equimolar quantities with, in some case, up to about 200% stoichiometrically calculated excess of the propiolic or tetrolic acid reagent. The reaction time is between 1 hour and 24 hours. After the reaction is terminated, which can be determined by thin layer chromatography (e.g. with silica gel and methanol-methylene chloride or chloroform), the product of formula IIa is recovered by conventional means, such as concentrating the solution, extraction, and chromatography. The solids are then purified by standard procedures e.g. crystallization, chromatography, extraction or the like.

Compounds of formula II with a 5-hydroxy or acyloxy substituent are produced from compounds of formula IIa. A selected compound of formula IIa is treated in the cold, −20° to +20° C., with an organic peracid. In the preferred embodiment of this invention the peracid is used in a solvent such as methanol, ethanol, ether, tetrahydrofuran and the like. As peracids, peracetic, performic, perpropionic, perbenzoic, m-chloroperbenzoic, pertoluic acid or the like can be used in equimolar to 3-4 equimolar quantities. The reaction period is from 2–24 hours in an ice bath followed by 2–24 hours at room temperature. The thus obtained 7-phenylpyrimido[1,2-a][1,4]benzodiazepin-3[5H]one 6-oxide IIb is recovered by conventional procedures, e.g. concentration of the mixture, extraction, and evaporation of the extracts.

The thus-obtained N-oxide IIb is treated with acetic anhydride, usually in a solvent such as acetic acid. The reaction is performed at elevated temperature 60°–120° C., preferably on a steam bath. The product, a 5-hydroxy-7-phenylpyrimido[1,2-a][1,4]benzodiazepin-3[5H]-one acetate IIc, is recovered by standard methods such as concentration, extraction, chromatography, and combinations thereof.

The free hydroxy compound, 5-hydroxy-7-phenylpyrimido[1,2-a][1,4]benzodiazepin-3[5H]-one IId is produced by a conventional base hydrolysis e.g. in water, methanol, ethanol, mixtures thereof or the like, in the presence of a base e.g. sodium or potassium hydroxide or carbonate. Compound IIc is obtained in pure form by methods, such as concentration, extraction, or the like.

If the desired compound II is a succinate, the free alcohol IId is esterified in the usual manner with succinic anhydride and the resulting product, can be treated with a diazoalkane, e.g. diazomethane or diazoethane and with sodium or potassium alkanoate.

Compounds of formulae II in which $R_o$ is hydroxymethyl are obtainable by reduction of compounds of formulae IIa wherein $R_o'$ is —COOR in which R is alkyl of 1 to 3 carbon atoms, inclusive. The reduction is preferably carried out with lithium aluminum hydride in stoichiometric relation to the starting material IIa at temperatures between 0°–40° C., preferably at room temperature.

The following preparation and examples are illustrative of the processes and products of the present invention, but are not to be construed as limiting.

PREPARATION

2-Amino-7-chloro-5-phenyl-3H-1,4-benzodiazepine

A solution of 2.87 g. (10 millimoles) of 7-chloro-1,3-dihydro-5-phenyl-2H-1,4-benzodiazepine-2-thione in 50 ml. of methanol saturated with ammonia gas was stirred at 24°–26° C. (room temperature) for 2½ hours. Crystallization occurred during stirring. The crystals of 2-amino-7-chloro-5-phenyl-3H-1,4-benzodiazepine were recovered by filtration and dried, yield 1.55 g. (57.5%) of 2-amino-7-chloro-5-phenyl-3H-1,4-benzodiazepine of melting point 236°–237° C.

Anal. calcd. for $C_{15}H_{12}ClN_3$: C, 66.79; H, 4.49; Cl, 13.15; N, 15.57. Found: C, 66.97; H, 4.53; Cl, 13.15; N, 15.49.

In the manner given above other 2-thiones are treated with ammoniacal methanol to give the corresponding 2-amino-5-phenyl-3H-1,4-benzodiazepines.

EXAMPLE 1

9-Chloro-7-phenylpyrimido[1,2-a][1,4]benzodiazepin-3(5H)-one

A mixture of 2-amino-7-chloro-5-phenyl-3H-1,4-benzodiazepine (8.07 g.; 0.03 mole), methyl propiolate (2.52 g.; 0.03 mole) and 150 ml. of methanol was refluxed 4 hours. The resulting solution was evaporated and the residue chromatographed on 2040 g. of silica gel using 3% methanol-chloroform as the eluent. Fractions 1–10 (400 ml. each) gave a trace. Fractions 11–17 (250 ml. each) were collected and gave 1.75 g. of a product a. Crystallization from ether afforded colorless prisms of compound A, of melting point 189°–190° C. unchanged on recrystallization.

Anal. calcd. for $C_{21}H_{21}ClN_2O_4$: C, 62.92; H, 5.28; Cl, 8.85; N, 6.99. Found: C, 63.09; H, 5.23; Cl, 8.86; N, 7.11.

Fraction 18 gave 0.061 g. which was discarded. Fractions 19–24 gave traces. Fractions 25–34 and fractions 35–37 (eluted with 6% methanol-94% methylene chloride) gave 1.8 g. of a product. Crystallization of this product from methylene ether gave 0.675 g. Thin layer chromatography showed this to be a mixture of two materials. It was, therefore, chromatographed on 135 g.

of silica gel using 3% methanol-97% chloroform as eluent. The first 460 ml. gave methylene chloride-methanol, but no material. The next 60 ml. gave 0.347 g. of product. Crystallization from methylene chloride-methanol gave 0.31 g. of compound B as pale yellow needles of melting point 231°–232° C.

Anal. calcd. for $C_{20}H_{19}ClN_2O_4$: C, 62.09; H, 4.95; Cl, 9.17; N, 7.24. Found: C, 61.80; H, 4.98; Cl, 9.37; N, 7.10.

The next 30 ml. gave a trace of material. The next 90 ml. afforded a compound C, which was crystallized from methyl chloride-ether to give 0.205 g. of a product of melting point 228° C. (dec.)

The original chromatography was continued with 6% methanol-94% methylene chloride. Fractions 38–39 gave a trace of material. Fractions 40–44 gave 0.949 g. of starting material. Elution was continued with 12% methanol-88% methylene chloride. Fractions 45–46 gave 0.301 g. of a mixture which was discarded. Fractions 47–55 gave 3.548 g. of a solid which was crystallized from methylene chloride-ether to give 2.358 g. of 9-chloro-7-phenylpyrimido[1,2-a][1,4]benzodiazepin-3(5H)-one of melting point 210°–211° C.

Anal. calcd. for $C_{18}H_{12}ClN_3O \cdot CH_3OH$: C, 64.50; H, 4.56; Cl, 10.02; N, 11.88. Found: C, 64.25; H, 4.53; Cl, 10.29; N, 11.83.

EXAMPLE 2

9-Chloro-7-phenylpyrimido[1,2-a][1,4]benzodiazepin-3(5H)-one

A mixture of 2-amino-7-chloro-5-phenyl-3H-1,4-benzodiazepine (2.69 g.; 0.01 mole), methyl propiolate (0.84 g.; 0.01 mole) and 50 ml. of methanol was stirred at room temperature for 2.5 hours. The suspension was then refluxed for 30 minutes, and the resulting solution allowed to stand overnight. It was evaporated and chromatographed as described before to give 0.294 g. of 9-chloro-7-phenylpyrimido[1,2-a][1,4]benzodiazepin-3[5H]-one as the methanol solvate.

EXAMPLE 3

9-chloro-7-phenylpyrimido[1,2-a][1,4]benzodiazepin-3(5H)-one

A mixture of 2-amino-7-chloro-5-phenyl-3H-1,4-benzodiazepine (1.33 g.; 5 mmole), methyl propiolate (0.42 g.; 5 mmole) and 25 ml. of ethanol was refluxed 4 hours and evaporated. The residue was chromatographed on 150 g. of silica gel in 5% methanol-chloroform (25 ml. fractions were collected). Fractions 1–4 gave no material. Fractions 10–12 gave 0.37 g. of 9-chloro-7-phenylpyrimido[1,2-a][1,4]benzodiazepin-3(5H)-one of melting point 208°–209° C. (from methylene chloride-ether).

Anal. calcd. for $C_{18}H_{12}ClN_3O$: Cl, 11.02; N, 13.05. Found: Cl, 10.98; N, 13.20.

EXAMPLE 4

9-Chloro-7-(o-chlorophenyl)pyrimido[1,2-a][1,4]benzodiazepin-3(5H)-one

In the manner given in Example 1, 2-amino-7-chloro-5-(o-chlorophenyl)-3H-1,4-benzodiazepine, methyl propiolate and methanol were refluxed. The mixture was chromatographed to give 9-chloro-7-(o-chlorophenyl)pyrimido[1,2-a][1,4]benzodiazepin-3(5H)-one.

EXAMPLE 5

9-fluoro-7-(o-fluorophenyl)pyrimido[1,2-a][1,4]benzodiazepin-3(5H)-one

In the manner given in Example 1, 2-amino-7-fluoro-5-(o-fluorophenyl)-3H-1,4-benzodiazepine, methyl propiolate and methanol were refluxed. The mixture was chromatographed to give 9-fluoro-7-(o-fluorophenyl)pyrimido[1,2-a][1,4]benzodiazepin-3(5H)-one.

EXAMPLE 6

9-chloro-7-(o-bromophenyl)pyrimido[1,2-a][1,4]benzodiazepin-3(5H)-one

In the manner given in Example 1, 2-amino-7-chloro-5-(o-bromophenyl)-3H-1,4-benzodiazepine, ethyl propiolate, and ethanol were refluxed. The mixture was chromatographed to give 9-chloro-7-(o-bromophenyl)pyrimido[1,2-a][1,4]benzodiazepin-3(5H)-one.

EXAMPLE 7

9-trifluoromethyl-7-phenylpyrimido[1,2-a][1,4]benzodiazepin-3(5H)-one

In the manner given in Example 1, 2-amino-7-trifluromethyl-5-phenyl-3H-1,4-benzodiazepine, propyl propiolate and propanol were refluxed. The mixture was chromatographed to give 9-trifluoromethyl-7-phenylpyrimido[1,2-a][1,4]benzodiazepin-3(5H)-one.

EXAMPLE 8

9-Nitro-7-(o-chlorophenyl)pyrimido[1,2-a][1,4]benzodiazepin-3(5H)-one

In the manner given in Example 1, 2-amino-7-nitro-5-(o-chlorophenyl)-3H-1,4-benzodiazepine, methyl propiolate and methanol were refluxed. The mixture was chromatographed to give 9-nitro-7-(o-chlorophenyl)pyrimido[1,2-a][1,4]benzodiazepin-3(5H)-one.

EXAMPLE 9

9-Cyano-7-(p-methylsulfonylphenyl)pyrimido[1,2-a][1,4]benzodiazepin-3(5H)-one

In the manner given in Example 1, 2-amino-7-cyano-5-(p-methylsulfonylphenyl)-3H-1,4-benzodiazepine, methyl propiolate and methanol were refluxed. The mixture was chromatographed to give 9-cyano-7-(p-methylsulfonylphenyl)pyrimido[1,2-a][1,4]benzodiazepin-3(5H)-one.

EXAMPLE 10

8-Methoxy-7-(2,4-diethoxyphenyl)pyrimido[1,2-a][1,4]benzodiazepin-3(5H)-one

In the manner given in Example 1, 2-amino-6-methoxy-5-(2,4-diethoxyphenyl)-3H-1,4-benzodiazepine, methyl propiolate and methanol were refluxed. The mixture was chromatographed to give 8-methoxy-7-(2,4-diethoxyphenyl)pyrimido[1,2-a][1,4]benzodiazepin-3(5H)-one.

EXAMPLE 11

8,10-Diethyl-7-(m-ethylphenyl)pyrimido[1,2-a][1,4]benzodiazepin-3(5H)-one

In the manner given in Example 1, 2-amino-6,8-diethyl-5-(m-ethylphenyl)-3H-1,4-benzodiazepine, ethyl propiolate and ethanol were refluxed. The mixture was chromatographed to give 8,10-diethyl-7-(m-ethylphenyl)pyrimido[1,2-a][1,4]benzodiazepin-3(5H)-one.

EXAMPLE 12

11-Acetylamino-7-(p-cyanophenyl)pyrimido[1,2-a][1,4]benzodiazepin-3(5H)-one

In the manner given in Example 1, 2-amino-9-acetylamino-5-(p-cyanophenyl)-3H-1,4-benzodiazepine, methyl propiolate and methanol were refluxed. The mixture was chromatographed to give 11-acetylamino-7-(p-cyanophenyl)pyrimido[1,2-a][1,4]benzodiazepin-3(5H)-one.

EXAMPLE 13

9-chloro-7-(2,6-difluorophenyl)pyrimido[1,2-a][1,4]benzodiazepin-3(5H)-one

In the manner given in Example 2, 2-amino-7-chloro-5-(2,6-difluorophenyl)-3H-1,4-benzodiazepine, methyl propiolate and methanol were refluxed. The mixture was chromatographed to give 9-chloro-7-(2,6-difluorophenyl)pyrimido[1,2-a][1,4]benzodiazepin-3(5H)-one.

EXAMPLE 14

9-methylsulfinyl-7-(o-fluorophenyl)pyrimido[1,2-a][1,4]benzodiazepin-3(5H)-one In the manner given in Example 1, 2-amino-7-methylsulfinyl-5-(o-fluorophenyl)-3H-1,4-benzodiazepine, methyl propiolate and methanol were refluxed. The mixture was chromatographed to give 9-methylsulfinyl-7-(o-fluorophenylpyrimido)[1,2-a][1,4]-benzodiazepin-3(5H)-one.

EXAMPLE 15

10-ethylthio-7-(m-fluorophenyl)pyrimido[1,2-a][1,4]benzodiazepin-3(5H)-one

In the manner given in Example 1, 2-amino-8-ethylthio-5-(m-fluorophenyl)-3H-1,4-benzodiazepine, ethyl propiolate and ethanol were refluxed. The mixture was chromatographed to give 10-ethylthio-7-(m-fluorophenyl)pyrimido[1,2-a][1,4]benzodiazepin-3(5H)-one.

EXAMPLE 16

9-Chloro-1-methyl-7-phenylpyrimido[1,2-a][1,4]benzodiazepin-3(5H)-one

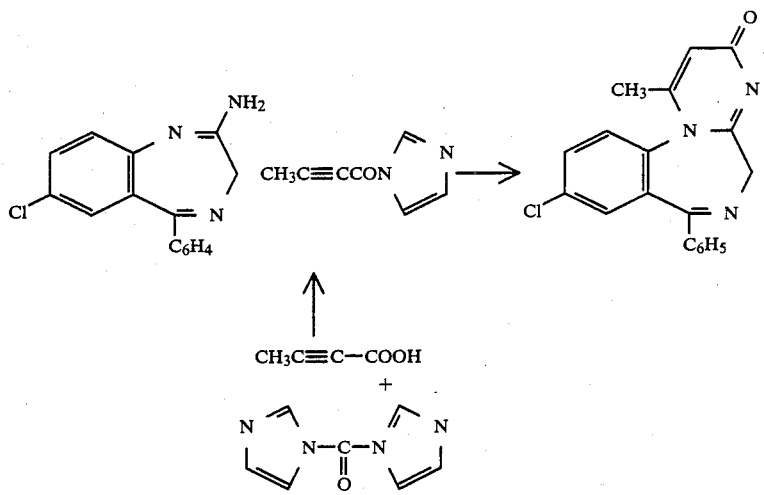

Carbonyldiimidazole (6.1 g.; 0.0375 mole) was added to a solution of tetrolic acid (3.15 g.; 0.0375 mole) in 50 ml. of tetrahydrofuran, and the mixture was stirred for 1 hour. A solution of 2-amino-7-chloro-5-phenyl-3H-1,4-benzodiazepine (10.1 g.; 0.0375 mole) in 50 ml. of dimethylformamide was added and the mixture stirred for 22 hours. It was evaporated at 38° C. (0.1 mm Hg), the residue was dissolved in methylene chloride water, the organic layer was washed thrice with water once with saturated salt solution, dried over anhydrous magnesium sulfate and evaporated. The residue (15.2 g.) was chromatographed on 2500 g. of silica gel in 5% methanol-95% chloroform. Fractions 1-26 (18.4 l.) gave only traces. Fractions 27-29 (100 ml. each) gave 1.597 g. (discarded). Fractions 30-31 (100 ml. each) gave 1.95 g. which was crystallized from methylene chloride to give 0.637 g. of desmethylvalium. Fractions 32-39 (100 ml. each) gave 2.996 g. which on re-chromatography gave 0.975 g. of desmethylvalium, 0.2 g. of the product 9-chloro-1-methyl-7-phenyl-pyrimido[1,2-a][1,4]benzodiazepin-3(5H)-one and 0.4 g. of a mixture of imidazole, starting material and product. Fractions 40-44 (100 ml. each) gave 1.1 g. (discarded). Fractions 45-46 (100 ml. each) gave 1.72 g. which was crystallized from methanol to give 0.214 g. of starting material. Fractions 47-56 (50 ml. each) gave 3.011 g. which was crystallized from methanol ether to give 1.277 g. of 9-chloro-1-methyl-7-phenylpyrimido[1,2-a][1,4]-benzodiazepin-3(5H)-one of melting point 237° C. dec.

Anal. calcd. for $C_{19}H_{14}ClN_3O$: C,67.96; H, 4.20; Cl, 10.56; N, 12.51. Found: C, 68.00; H, 4.36; Cl, 10.66; N, 12.46.

EXAMPLE 17

9-Chloro-1-ethyl-7-(o-chlorophenyl)pyrimido[1,2-a][1,4]benzodiazepin-3(5H)-one In the manner given in Example 16 carbonyldiimidazole β-pentynoic acid and 2-amino-7-chloro-5-(o-chlorophenyl)-3H-1,4-benzodiazepine were stirred in tetrahydrofuran-di-methylformamide to give 9-chloro-1-ethyl-7-(o-chlorophenyl) pyrimido[1,2-a][1,4]benzodiazepin-3(5H)-one.

EXAMPLE 18

9-Nitro-1-propyl-7-(2,6-difluorophenyl)pyrimido[1,2-a][1,4]benzodiazepin-3(5H)-one.

In the manner given in Example 16, carbonyldiimidazole, p-hexynoic acid and 2-amino-7-nitro-5-(2,6-difluorophenyl)-3H-1,4-benzodiazepine were stirred in tetrahydrofuran-dimethylformamide to give 9-nitro-1-propyl-7-(2,6-difluorophenyl)pyrimido[1,2-a][1,4]benzodiazepin-3(5H)-one.

EXAMPLE 19

9-Nitro-1-methyl-7-(o-chlorophenyl)pyrimido[1,2-a][1,4]benzodiazepin-3(5H)-one

In the manner given in Example 16, carbonyldiimidazole tetrolic acid and 2-amino-7-nitro-5-(o-chlorophenyl)-3H-1,4-benzodiazepine were stirred in tetrahydrofuran-dimethylformamide to give 9-nitro-1-methyl-7-(o-chlorophenyl)pyrimido[1,2-a][1,4]-benzodiazepin-3(5H)-one.

EXAMPLE 20

10-ethylthio-1,9-diethyl-7-(p-methylphenyl)-pyrimido[1,2-a][1,4]-benzodiazepin-3-one In the manner given in Example 16, carbonyldiimidazole, 3-pentynoic acid and 2-amino-8-ethylthio-7-ethyl-5-(p-methylphenyl)-3H-1,4-benzodiazepine were stirred in tetrahydrofuran-dimethylformamide to give 10-ethylthio 1,9-diethyl-7-(p-methylphenyl)-pyrimido[1,2-a][1,4]benzodiazepin-3(5H)-one.

EXAMPLE 21

9-Chloro-1-[(dimethylaminomethyl)]-7-phenyl-pyrimido[1,2-a][1,4]benzodiazepin-3(5H)-one In the manner given in Example 16, carbonyldiimidazole, 4-dimethylamino-butyn-2-oic acid and 2-amino-7-chloro-5-phenyl-3H-1,4-benzodiazepine was stirred in tetrahydrofuran-dimethylformamide to give 9-chloro-1(dimethylaminoethyl)-7-phenylpyrimido[1,2-a][1,4]-benzodiazepin-3(5H)-one.

EXAMPLE 22

9-chloro-1-(dimethylaminoethyl)-7-[(o-chlorophenyl)-pyrimido][1,2-a][1,4]benzodiazepin-3(5H)-one In the manner given in Example 21, carbonyldiimidazole, 5-dimethylamino-2-pentynoic acid, and 2-amino-7-chloro-5-(o-chlorophenyl)-3H-1,4-benzodiazepine were stirred in tetrahydrofuran-dimethylformamide to give 9-chloro-1-(dimethylaminoethyl)-7-[(o-chlorophenyl)pyrimido][1,2-a][1,4]benzodiazepin-3(5H)-one.

EXAMPLE 23

9-Nitro-1-(3-diethylaminopropyl)-7-(2,6-difluorophenyl)pyrimido[1,2-a][1,4]benzodiazepin-3(5H)-one.

In the manner given in Example 21, carbonyldiimidazole, 6-diethylamino-2-hexynoic acid and 2-amino-7-nitro5-(2,6-difluorophenyl)-3H-1,4-benzodiazepine was stirred in tetrahydrofuran-dimethylformamide to give 9-nitro-1-(3-diethylaminopropyl)-7-(2,6-difluorophenyl)pyrimido[1,2-a][1,4]benzodiazepin-3(5H)-one.

EXAMPLE 24

10-Ethylthio-9-ethyl-1-(1-pyrrolidinylmethyl)7-(p-methylphenyl)pyrimido[1,2-a][1,4]-benzodiazepin-3(5H)-one In the manner given in Example 21, carbonyldiimidazole, 4-(1-pyrrolidinyl)tetrolic acid, and 2-amino-8-ethylthio-7-ethyl-5-(p-methylphenyl)-3H-1,4-benzodiazepine was stirred in tetrahydrofuran-dimethylformamide to give 10-ethylthio-9-ethyl-1-(1-pyrrolidinylmethyl)-7-(p-methylphenyl)pyrimido[1,2-a][1,4]benzodiazepin-3(5H)-one.

EXAMPLE 25

9-Cyano-1-(1-morpholinylethyl)-7-(o-chlorophenyl)-pyrimido[1,2-a][1,4]benzodiazepin-3(5H)-one In the manner given in Example 21, carbonyldiimidazole, 5-(1-morpholinyl)-2-pentynoic acid, and 2-amino-7-cyano-5-(o-chlorophenyl)-3H-1,4-benzodiazepine was stirred in tetrahydrofuran-dimethylformamide to give 9-cyano-1-(1-morpholinylethyl)-7-(o-chlorophenyl)pyrimido[1,2-a][1,4]benzodiazepin-3(5H)-one.

EXAMPLE 26

8-Methoxy-1-[1-(4-methylpiperazinyl)propyl]-7-(o-fluorophenyl)pyrimido[1,2-a][1,4]benzodiazepin-3(5H)-one In the manner given in Example 21, carbonyldiimidazole, 6-(4-methylpiperazinyl)-2-hexynoic acid, and 2-amino-6-methoxy-5-(o-fluorophenyl)-3H-1,4-benzodiazepine was stirred in tetrahydrofuran-dimethylformamide to give 8-methoxy-1-[1-(4-methylpiperazinyl)propyl]-7-(o-fluorophenyl)pyrimido[1,2-a][1,4]benzodiazepin-3(5H)-one.

EXAMPLE 27

1-Carbomethoxy-9-chloro-7-phenylpyrimido[1,2-a][1,4]benzodiazepin-3(5H)-one

A mixture of 2-amino-7-chloro-5-phenyl-3H-1,4-benzodiazepine (13.5 g.; 0.05 mole), dimethyl acetylenedicarboxylate (7.1 g.; 0.05 mole) and 250 ml. of methanol were refluxed for 2 hours and evaporated. The residue was dissolved in 50 ml. of methylene chloride and chromatographed on 2 kg. of silica gel using 60% ethyl acetate 40% cyclohexane. Fractions 1–6 (4.5 l.) gave no material. Fractions 6–51 were discarded. Fraction 52–54 gave 6.3 g. of solids which were crystallized from methylene chloride ether to give 1-carbomethoxy-9-chloro-7-phenylpyrimido[1,2-a][1,4]benzodiazepin-3(5H)-one 3.1 g. of melting point 214°–215° C. dec., raised to 216°–217° C. on recrystallization from methanol-ether.

Anal. calcd. for $C_{20}H_{14}ClN_3O_3$: C, 63.25; H, 3.72; Cl, 9.33; N, 11.06. Found: C, 63.12; H, 3.96; Cl, 9.13; N, 10.80.

EXAMPLE 28

1-Carbomethoxy-9-chloro-7-(o-chlorophenyl)-pyrimido[1,2-a][1,4]benzodiazepin-3(5H)-one In the manner given in Example 21, 2-amino-7-chloro-5-(o-chlorophenyl)-3H-1,4-benzodiazepine was heated in methanol with dimethyl acetylenedicarboxylate to give 1-carbomethoxy-9-chloro-7-(o-chlorophenyl)pyrimido[1,2-a][1,4]benzodiazepin-3(5H)-one.

EXAMPLE 29

1-carboethoxy-9-nitro-7-(o-chlorophenyl)pyrimido[1,2-a][1,4]benzodiazepin-3(5H)-one In the manner given in Example 27, 2-amino-7-nitro-5-(o-chlorophenyl)-3H-1,4-benzodiazepine was heated in ethanol with diethyl acetylenedicarboxylate to give 1-carboethoxy-9-nitro-7-(o-chlorophenyl)pyrimido[1,2-a][1,4]benzodiazepin-3(5H)-one.

EXAMPLE 30

1-Carbopropoxy-9-chloro-7-(2,6-difluorophenyl)-pyrimido[1,2-a][1,4]benzodiazepin-3(5H)-one In the manner given in Example 27, 2-amino-7-chloro-5-(2,6-difluorophenyl)-3H-1,4-benzodiazepine was heated in propanol with dipropyl acetylenedicarboxylate to give 1-carbopropoxy-9-chloro-7-(2,6-difluorophenyl)pyrimido[1,2-a][1,4]benzodiazepin-3(5H)-one.

EXAMPLE 31

1-carboethoxy-9,10-dimethyl-7-(p-fluorophenyl)-pyrimido[1,2-a][1,4]benzodiazepin-3(5H)-one In the manner given in Example 27, 2-amino-7,8-dimethyl-5-(p-fluorophenyl)-3H-1,4-benzodiazepine was heated in ethanol with diethyl acetylenedicarboxylate to give 1-carboethoxy-9,10-dimethyl-7-(p-fluorophenyl)pyrimido[1,2-a][1,4]benzodiazepin-3(5H)-one.

EXAMPLE 32

9-Chloro-7-phenylpyrimido[1,2-a][1,4]benzodiazepin-3(5H)-one

A mixture of 1-carbomethoxy-9-chloro-7-phenylpyrimido[1,2-a][1,4]benzodiazepin-3(5H)-one (1.02 g.; 2.7 mmole), lithium iodide (2.16 g.; 16.2 mmole) and 54 ml. of pyridine was refluxed for 75 minutes. It was then evaporated, water and methylene chloride were added and the organic layer was separated and washed with saturated salt solution, dried over anhydrous magnesium sulfate and evaporated. The residue (0.607 g.) was chromatographed on 60 g. of silica gel using a mixture of 5% methanol-95% chloroform as eluent. Fractions 1–7 (800 ml. total) gave no material. Fractions 8–12 (500 ml. total) gave 0.454 g. of 9-chloro-7-phenylpyrimido[1,2-a][1,4]benzodiazepin-3(5H)-one. Crystallization from methylene chloride ether gave 0.3 g. of 9-chloro-7-phenylpyrimido[1,2-a][1,4]benzodiazepin-3(5H)-one of melting point 208°–209° C. It was identical to the sample prepared from 2-amino-7-chloro-5-phenyl-3H-1,4-benzodiazepine and methyl propiolate.

EXAMPLE 33

9-Chloro-7-(o-chlorophenyl)pyrimido[1,2-a][1,4]benzodiazepin-3(5H)-one

In the manner given in Example 32, 1-carboethoxy-9-chloro-7-(o-chlorophenyl)pyrimido[1,2-a][1,4]benzodiazepin-3(5H)-one was heated in pyridine with lithium iodide to give 9-chloro-7-(o-chlorophenyl)pyrimido[1,2-a][1,4]benzodiazepin-3(5H)-one.

EXAMPLE 34

9-Nitro-7-(o-chlorophenyl)pyrimido[1,2-a][1,4]benzodiazepin-3(5H)-one

In the manner given in Example 32, 1-carbomethoxy-9-nitro-7-(o-chlorophenyl)pyrimido[1,2-a][1,4]benzodiazepin3(5H)-one was heated in pyridine with lithium iodide to give 9-nitro-7-(o-chlorophenyl)pyrimido[1,2-a][1,4]benzodiazepin-3(5H)-one.

EXAMPLE 35

9-Chloro-7-(2,6-difluorophenyl)pyrimido[1,2-a][1,4]benzodiazepin-3(5H)-one

In the manner given in Example 32, 1-carbopropoxy-9-chloro-7-(2,6-difluorophenyl)pyrimido[1,2-a][1,4]benzodiazepine-3(5H)-one was heated in pyridine with lithium iodide to give 9-chloro-7-(2,6-difluorophenyl)-pyrimido[1,2-a][1,4]benzodiazepin-3(5H)-one.

EXAMPLE 36

8,10-Dimethyl-7-(p-fluorophenyl)pyrimido[1,2-a][1,4]benzodiazepin-3(5H)-one

In the manner given in Example 32, 1-carboethoxy-8,10-dimethyl-7-(p-fluorophenyl)pyrimido[1,2-a][1,4]benzodiazepin-3(5H)-one was heated in pyridine with lithium iodide to give 8,10-dimethyl-7-(p-fluorophenyl)pyrimido[1,2-a][1,4]benzodiazepin-3(5H)-one.

EXAMPLE 37

1-Hydroxymethyl-9-chloro-7-phenylpyrimido[1,2-a][1,4]benzodiazepin-3(5H)-one

A solution of 1 mmole of 1-carbomethoxy-9-chloro-7-phenylpyrimido[1,2-a][1,4]benzodiazepin-3(5H)-one in tetrahydrofuran was reacted at room temperature with the stoichiometric amount of lithium aluminum hydride and stirred for several hours. It was decomposed with water and 15% sodium hydroxide and worked up to give 1-hydroxymethyl-9-chloro-7-phenylpyrimido[1,2-a][1,4]benzodiazepin-3(5H)-one.

EXAMPLE 38

1-Hydroxymethyl-9-chloro-7-(o-chlorophenyl)-pyrimido[1,2-a][1,4]benzodiazepin-3(5H)-one In the manner given in Example 37, 1-carbomethoxy-9-chloro-7-(o-chlorophenyl)pyrimido[1,2-a][1,4]benzodiazepin-3(5H)-one was reduced with lithium aluminum hydride to give 1-hydroxymethyl-9-chloro-7-(o-chlorophenyl)pyrimido[1,2-a][1,4]benzodiazepin-3(5H)-one.

EXAMPLE 39

1-Hydroxymethyl-9-chloro-7-(2,6-difluorophenyl)-pyrimido[1,2-a][1,4]benzodiazepin-3(5H)-one In the manner given in Example 37, 1-carbomethoxy-9-chloro-7-(2,6-difluorophenyl)pyrimido[1,2-a][1,4]benzodiazepin-3(5H)-one was reduced with lithium aluminum hydride to give 1-hydroxmethyl-9-chloro-7-(2,6-difluorophenyl)pyrimido[1,2-a][1,4]benzodiazepin-3(5H)-one.

In the manner given in the preceding Examples other compounds of formula II can be produced by reacting a 2-amino-5-phenyl-3H-1,4-benzodiazepine with the proper acetylenecarboxylate as described by Methods I, II, or III above. Representative compounds, thus produced, comprise:

9-cyano-7-[(p-dipropylamino)phenyl]pyrimido[1,2-a][1,4]benzodiazepin-3(5H)-one;
10-chloro-7-phenylpyrimido[1,2-a][1,4]benzodiazepin-3(5H)-one;
1-methyl-8-chloro-7-(m-bromophenyl)pyrimido[1,2-a][1,4]benzodiazepin-3(5H)-one;

1-ethyl-9-chloro-7-(3,4-dimethyl)phenylpyrimido[1,2-a][1,4]benzodiazepin-3(5H)-one;
1-propyl-7-phenylpyrimido[1,2-a][1,4]benzodiazepin-3(5H)-one;
9-bromo-7-phenylpyrimido[1,2-a][1,4]benzodiazepin-3(5H)-one;
1-methyl-7-[(2-methyl-4-methoxyphenyl]pyrimido[1,2-a][1,4]benzodiazepin-3(5H)-one;
11-bromo-7-phenylpyrimido[1,2-a][1,4]benzodiazepin-3(5H)-one;
7-phenylpyrimido[1,2-a][1,1]benzodiazepin-3(5H)-one;
1-methyl-9-cyano-7-phenylpyrimido[1,2-a][1,4]benzodiazepin-3(5H)-one;
10-cyano-7-phenylpyrimido[1,2-a][1,4]benzodiazepin-3(5H)-one;
9-chloro-7-(o-chlorophenyl)pyrimido[1,2-a][1,4]benzodiazepin-3(5H)-one;
1-ethyl-8-ethylthio-7-(o-bromophenyl)pyrimido[1,2-a][1,4]benzodiazepin-3(5H)-one;
1-methyl-8,10-dichloro-7-(o-fluorophenyl)-pyrimido[1,2-a][1,4]benzodiazepin-3(5H)-one;
10-propoxy-9-bromo-7-[m-(ethylsulfinyl)phenyl]-pyrimido[1,2-a][1,4]benzodiazepin-3(5H)-one;
11-diisopropylamino-9-methyl-7-[m-(propylsulfonyl)-phenyl]pyrimido[1,2-a][1,4]benzodiazepin-3(5H)-one;
1-ethyl-9-iodo-7-(o-fluorophenyl)pyrimido[1,2-a][1,4]benzodiazepin-3(5H)-one;
9-methyl-7-(o-fluorophenyl)pyrimido[1,2-a][1,4]benzodiazepin-3(5H)-one;
10-nitro-7-(o-chlorophenyl)pyrimido[1,2-a][1,4]benzodiazepin-3(5H)-one;
9-bromo-7-(o-bromophenyl)pyrimido[1,2-a][1,4]benzodiazepin-3(5H)-one;
1-methyl-9-dimethylamino-7-phenylpyrimido[1,2-a][1,4]benzodiazepin-3(5H)-one;
8,11-dichloro-7-(p-isopropylphenyl)pyrimido[1,2-a][1,4]-benzodiazepin-3(5H)-one;
8,10-diethyl-7-(m-ethylphenyl)pyrimido[1,2-a][1,4]benzodiazepin-3(5H)-one;
1-propyl-8-nitro-7-(p-cyanophenyl)pyrimido[1,2-a][1,4]-benzodiazepin-3(5H)-one;
11-acetylamino-7-(p-cyanophenyl)pyrimido[1,2-a][1,4]benzodiazepin-3(5H)-one;
1-hydroxymethyl-9-nitro-7-[(o-chlorophenyl)-pyrimido][1,2-a][1,4]benzodiazepin-3(5H)-one;
1-dimethylaminopropyl-9-nitro-7-[(o-chlorophenyl)-pyrimido][1,2-a][1,4]benzodiazepin-3(5H)-one;
1-dimethylaminomethyl-9-chloro-7-[(o-chlorophenyl)-pyrimido][1,2-a][1,4]benzodiazepin-3(5H)-one;
and the like.

EXAMPLE 40

9-Chloro-7-phenylpyrimido[1,2-a][1,4]benzodiazepin-3(5H)-one6-N-oxide

A stirred solution of 9-chloro-7-phenylpyrimido[1,2-a][1,4]benzodiazepin-3(5H)-one (1.0 g.; 3.0 millimoles) in absolute ethanol, in an ice bath, was treated with m-chloroperbenzoic acid (1.0 g.; 6.0 millimoles). The mixture was allowed to stand in the ice bath for 8 hours and at room temperature, about 24° C., for 18 hours. It was then concentrated in vacuo, the residue suspended in aqueous, cold, dilute potassium carbonate solution and extracted with methylene chloride. The extract was washed with water, dried and concentrated in vacuo.

The residue was chromatographed on 100 g. of silica gel taking 50 ml. fractions. The desired product was eluted in fractions 50-70 using 10% methanol-90% ethyl acetate. The product, 9-chloro-7-phenyl-pyrimido[1,2-a][1,4]benzodiazepin-3(5H)-one 6-N-oxide was isolated by concentration of the chromatographic fraction.

EXAMPLE 41

9-Chloro-5-hydroxy-7-phenylpyrimido[1,2-a][1,4]benzodiazepin-3(5H)-one acetate

A stirred mixture of 9-chloro-7-phenylpyrimido[1,2-a][1,4]benzodiazepin-3(5H)-one 6-N-oxide (704 mg.; 2.0 mmoles), acetic anhydride (4.0 ml.) and acetic acid (2.5 ml.) was warmed on the steam bath, under nitrogen, for 30 minutes and concentrated in vacuo. The residue was suspended in water, neutralized with sodium carbonate and extracted with methylene chloride. The extract was dried, concentrated and chromatographed on silica gel eluting with ethyl acetate to yield 9-chloro-5-hydroxy-7-phenylpyrimido-[1,2-a][1,4]benzodiazepin-3(5H)-one acetate.

EXAMPLE 42

9-Chloro-5-hydroxy-7-phenylpyrimido[1,2-a][1,4]benzodiazepin-3(5H)-one

A stirred suspension of 9-chloro-5-hydroxy-7-phenyl-pyrimido[1,2-a][1,4]benzodiazepin-3(5H)-one acetate (394 mg.; 1 millimole) in absolute ethanol (25 ml.), under nitrogen, was stirred for 3 hours at room temperature (23° C.) with 2.2 ml. of 0.5N aqueous sodium hydroxide, poured into water and extracted with methylene chloride. The extract was dried and concentrated and the residue chromatographed on silica gel, eluting with ethyl acetate to yield 200 mg. 9-chloro-5-hydroxy-7-phenylpyrimido[1,2-a][1,4]benzodiazepin-3(5H)-one.

EXAMPLE 43

9-Chloro-5-hydroxy-7-phenylpyrimido[1,2-a][1,4]benzodiazepin-3(5H)-one hemisuccinate and its methyl ester A suspension of 9-chloro-5-hydroxy-7-phenyl-pyrimido[1,2-a][1,4]benzodiazepin-3(5H)-one in pyridine was stirred for 3 hours with succinic anhydride. The mixture was then poured in ice water, the solid collected on filter and recrystallized from methanol-water to give 9-chloro-5-hydroxy-7-phenyl-pyrimido[1,2-a][1,4]benzodiazepin-3(5H)-one hemisuccinate.

Treatment of this hemisuccinate with diazomethane gave methyl 9-chloro-5-hydroxy-7-phenylpyrimido[1,2-a][1,4]benzodiazepin-3(5H)-one succinate.

EXAMPLE 44

9-Chloro-7-(o-chlorophenyl)pyrimido[1,2-a][1,4]benzodiazepin-3(5H)-one-6-N-oxide In the manner given in Example 40, 9-chloro-7-(o-chlorophenyl)pyrimido[1,2-a][1,4]benzodiazepin-3(5H)-one was treated with m-chloroperbenzoic acid to give 9-chloro-7-(o-chlorophenyl)pyrimido[1,2-a][1,4]benzodiazepin-3(5H)-one-6-N-oxide.

EXAMPLE 45

9-Chloro-5-hydroxy-7-(o-chlorophenyl)pyrimido[1,2-a][1,4]benzodiazepin-3(5H)-one acetate In the manner given in Example 41, 9-chloro-7-(o-chlorophenyl)pyrimido[1,2-a][1,4]benzodiazepin-3(5H)-one 6-N-oxide was treated with acetic anhydride in acetic acid to give 9-chloro-5-hydroxy-7-(o-chlorophenyl)-pyrimido[1,2-a][1,4]benzodiazepin-3(5H)-one acetate.

EXAMPLE 46

9-Chloro-5-hydroxy-7-(o-chlorophenyl)pyrimido-[1,2-a][1,4]benzodiazepin-3(5H)-one In the manner given in Example 42, 9-chloro-5-hydroxy-7-(o-chlorophenyl)pyrimido[1,2-a][1,4]benzodiazepin-3(5H)-one acetate was hydrolyzed in ethanol with aqueous sodium hydroixde to give 9-chloro-5-hydroxy-7-(o-chlorophenyl)pyrimido[1,2-a][1,4]benzodiazepin-3(5H)-one.

EXAMPLE 47

9-Chloro-5-hydroxy-7-(o-chlorophenyl)pyrimido-[1,2-a][1,4]benzodiazepin-3(5H)-one propionate To a solution of 9-chloro-5-hydroxy-7-(o-chlorophenyl)pyrimido[1,2-a][1,4]benzodiazepin-3(5H)-one in pyridine was added propionic anhydride. The mixture was allowed to stand at room temperature for 6 hours and was then poured into ice water. The solids thus produced were recovered by filtration and recrystallized from methanol to give 9-chloro-5-hydroxy-7-(o-chlorophenyl)pyrimido[1,2-a][1,4]benzodiazepin-3(5H)-one propionate.

EXAMPLE 48

9-Chloro-5-hydroxy-7-(o-chlorophenyl)pyrimido[1,2-a][1,4]benzodiazepin-3(5H)-one hemisuccinate and its ethyl ester In the manner given in Example 43, 9-chloro-5-hydroxy-7-(o-chlorophenyl)pyrimido[1,2-a][1,4]benzodiazepin-3(5H)-one was treated with succinic anhydride to give 9-chloro-5-hydroxy-7-(o-chlorophenyl)-pyrimido[1,2-a][1,4]benzodiazepin-3(5H)-one hemisuccinate.

Treatment of this hemisuccinate with diazoethane gave ethyl 9-chloro-5-hydroxy-7-(o-chlorophenyl)-pyrimido[1,2-a][1,4]benzodiazepin-3(5H)-one succinate.

Other compound of formula IIa, shown in the preceding examples and list can be converted to the 5-substituted compounds by treatment of the compounds of formula IIa above, with an organic peracid (Example 16) to give the corresponding 6-N-oxides IIb of these compounds. Such N-oxides by treatment with acetic anhydride give the 5-acetoxy compounds of formula IIc; which by saponification give the 5-hydroxy analogues IId. The latter compounds of formula IId can be esterified with acid anhydrides in conventional manner, as illustrated in examples 43, 47, and 48. In this manner the propionates and hemisuccinates of the compounds of the prior examples and the list are obtained. The hemisuccinates may further be converted to the alkyl esters by treatment with diazoalkanes.

The compounds of formula II (IIa, IIb, IIc, IId, and IIe) may further be converted to their pharmacologically acceptable acid addition salts by reaction with stoichiometrically calculated amounts of selected acids in water, ethanol, or ether. In this manner the hydrochlorides, hydrobromides, hydriodides, sulfates, phosphates, acetates, propionates, lactates, tartrates, citrates, maleates, malates, pamoates, benzenesulfonates, p-toluenesulfonates, methanesulfonates, cyclohexanesulfamates, salicylates, naphthalene-$\beta$-sulfonates, and the like of the foregoing 7-phenylpyrimido[1,2-a][1,4]benzodiazepin-3-ones of formula II (IIa, IIb, IIc, IId, and IIe) are obtained.

I claim:

1. A phenylpyrimido[1,2-a][1,4]benzodiazepin-3(5H)-one of the formula

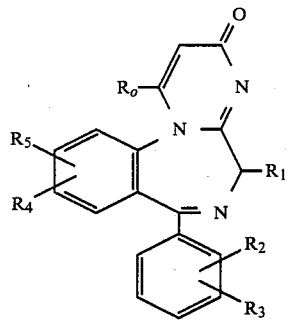

wherein $R_0$ is selected from the group consisting of hydrogen, alkyl of 1 to 3 carbon atoms, inclusive, hydroxymethyl, —COOR in which R is alkyl defined as above, and

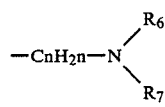

in which n is a number of 1 to 4 and $R_6$ and $R_7$ are alkyl defined as above; wherein $R_1$ is selected from the group consisting of hydrogen, hydroxy, acetoxy, propionoxy, —OCO—CH$_2$—CH$_2$COOH, —OCO—CH$_2$—CH$_2$—COOR in which R is alkyl defined as above; wherein $R_2$, $R_3$, $R_4$ and $R_5$ are selected from the group consisting of hydrogen, halogen, nitro, cyano, trifluoromethyl, and alkyl and alkoxy, in which the carbon moiety is of 1 to 3 carbon atoms, inclusive, and dialkylamino in which alkyl is defined as above, and the pharmacologically acceptable acid addition salts and N-oxides thereof, with the proviso that the compound cannot be 9-chloro-7-(2-chlorophenyl)-3,5-dihydro-1-methyl-pyrimido-(1,2-a)(1,4)benzodiazepin-3-one.

2. A 7-phenylpyrimido[1,2-a][1,4]benzodiazepin-3(5H)-one, according to claim 1, of the formula:

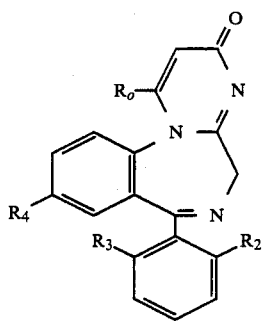

wherein $R_0$ is selected from the group consisting of hydrogen, alkyl of 1 to 3 carbon atoms, inclusive, hydroxymethyl, —COOR in which R is alkyl defined as above, and

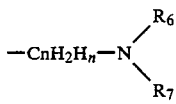

in which n is a number from 1 to 4, $R_6$ and $R_7$ are alkyl defined as above; wherein $R_2$, $R_3$ and $R_4$ are selected from the group consisting of hydrogen, trifluoromethyl, nitro, chloro, fluoro, or cyano.

3. A phenylpyrimido[1,2-a][1,4]benzodiazepin-3(5H)-one, according to claim 1 of the formula

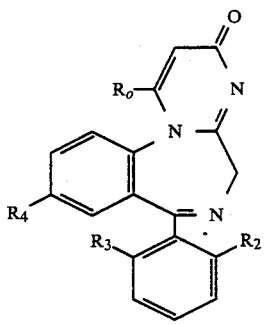

wherein $R_0$ is selected from the group consisting of hydrogen, alkyl of 1 to 3 carbon atoms, inclusive, hydroxymethyl, —COOR in which R is alkyl defined as above, and

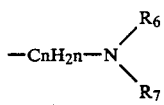

in which n is a number from 1 to 4, $R_6$ and $R_6$ are alkyl defined as above; wherein $R_2$, $R_3$ and $R_6$ are selected from the group consisting of hydrogen and chlorine.

4. A compound according to claim 3 wherein $R_0$, $R_2$, and $R_3$ are hydrogen and $R_4$ is chlorine and the compound is therefore 9-chloro-7-phenylpyrimido[1,2-a][1,4]benzodiazepin-3(5H)-one.

5. A compound according to claim 3 wherein $R_2$ and $R_4$ are chlorine and $R_0$ and $R_3$ are hydrogen and the compound is therefore 9-chloro-7-(o-chlorophenyl)-pyrimido[1,2-a][1,4]benzodiazepin-3(5H)-one.

6. A compound according to claim 3 wherein $R_0$ is methyl, $R_2$ and $R_3$ are hydrogen, $R_4$ is chloro and the compound is therefore 1-methyl-9-chloro-7-phenyl-pyrimido[1,2-a][1,4]benzodiazepin-3(5H)-one.

7. A compound according to claim 2, wherein $R_0$ is methyl, $R_2$ is chloro, $R_3$ is hydrogen, $R_4$ is nitro, and the compound is therefore 1-methyl-9-nitro-7-(o-chlorophenyl)pyrimido[1,2-a][1,4]benzodiazepin-3(5H)-one.

8. A compound according to claim 2 wherein $R_0$ is hydroxymethyl, $R_2$, $R_3$, and $R_5$ are hydrogen, $R_4$ is chloro, and the compound is therefore 9-chloro-1-hydroxymethyl-7-phenylpyrimido[1,2-a][1,4]benzodiazepin-3(5H)-one.

9. A compound according to claim 1 wherein $R_0$ is hydroxymethyl, $R_1$, $R_3$, and $R_5$ are hydrogen, $R_2$ is chloro; $R_4$ is chloro and the compound is therefor 9-chloro-1-hydroxymethyl-7-[(o-chlorophenyl)-pyrimido][1,2-a][1,4]benzodiazepin-3(5H)-one.

10. A compound according to claim 3, wherein $R_0$ is dimethylaminomethyl, $R_2$ and $R_3$ are hydrogen, $R_4$ is chloro and the compound is therefore 9-chloro-1-[(dimethylamino)methyl]-7-phenylpyrimido[1,2-a][1,4]benzodiazepin-3(5H)-one.

11. A compound according to claim 2 wherein $R_0$ is dimethylaminomethyl, $R_3$ is hydrogen; $R_2$ and $R_4$ are chloro and the compound is therefore 9chloro-1-[(dimethylamino)methyl]-7-[(o-chlorophenyl)pyrimido][1,2-a][1,4]benzodiazepin-3(5H)-one.

12. A compound according to claim 2 wherein $R_0$ is —COOCH$_3$; $R_2$ and $R_3$ are hydrogen and $R_4$ is chlorine, and the compound is therefore 1-carbomethoxy-9-chloro-7-phenylpyrimido[1,2-a][1,4]benzodiazepin-3(5H)-one.

13. A compound according to claim 2 wherein $R_0$ is —COOCH$_3$, $R_3$ is hydrogen, $R_2$ and $R_4$ are chlorine, and the compound is therefore 1-carbomethoxy-9-chloro-7-(o-chlorophenyl)pyrimido[1,2-a][1,4]benzodiazepin-3(5H)-one.

14. A compound of the formula

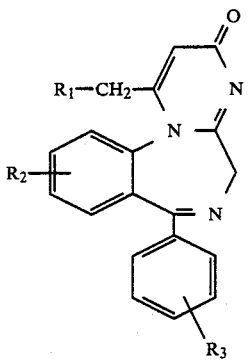

wherein $R_1$ is H or alkyl of 1 to 2 carbons, $R_2$ and $R_3$ are hydrogen, halogen, nitro, —CF$_3$, alkyl of 1 to 3 carbons, alkoxy of 1 to 3 carbons; the 6-position N-oxide and the pharmaceutically acceptable acid addition salts thereof.

15. A compound according to claim 1 wherein $R_2$ and $R_3$ are hydrogen.

16. A compound according to claim 2 wherein $R_2$ and $R_3$ are hydrogen.

17. A compound according to claim 14 wherein $R_3$ is hydrogen.

18. A process for the production of a compound of the formula IIa:

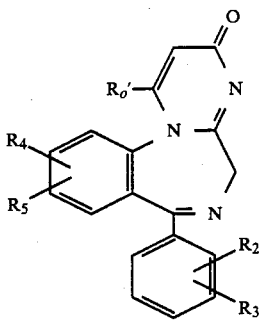

IIa wherein $R'_0$ is selected from the group consisting of hydrogen, alkyl of 1 to 3 carbon atoms, inclusive, —COOR in which R is alkyl defined as above; and

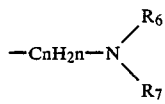

in which n is a number from 1 to 4 and $R_6$ and $R_7$ are alkyl defined as above; wherein $R_2$, $R_3$, $R_4$ and $R_5$ are selected from the group consisting of hydrogen, halogen, nitro, cyano, trifluoromethyl and alkyl, alkoxy and alkanoylamino in which the carbon moiety is 1 to 3 carbon atoms, inclusive, and dialkylamino in which alkyl is defined as above, which comprises: heating a compound of formula I

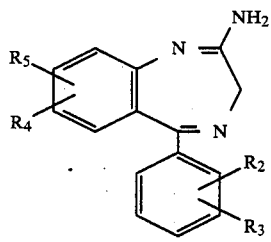

I wherein $R_2$, $R_3$, $R_4$ and $R_5$ are defined as above, with a reagent selected from the group acetylenic compounds consisting of HC≡C—COOR, and ROOC—C≡C—COOR in which R is alkyl of 1 to 3 carbon atoms, inclusive, and

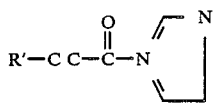

in which R' is alkyl defined as above, or is

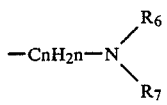

defined as above to obtain the compound of formula IIa above.

19. The process of claim 18, wherein as solvent methanol is used.

20. The process of claim 18 wherein the reagent is methyl propiolate.

21. The process of claim 18 wherein the starting material is 2-amino-7-chloro-5-phenyl-3H-1,4-benzodiazepine.

22. The process of claim 18 wherein the starting material is 2-amino-7-chloro-5-(o-chlorophenyl)-3H-1,4-benzodiazepine.

23. The process of claim 18 wherein the reagent is ROOC—C≡C—COOR and the product is therefore a 1-alkyloxycarbonyl-7-phenylpyrimido[1,2-a][1,4]benzodiazepin-3(5H)-one.

* * * * *